United States Patent
Abe

(10) Patent No.: US 10,426,425 B2
(45) Date of Patent: Oct. 1, 2019

(54) CONTROL DEVICE, CONTROL SYSTEM, RADIATION IMAGING SYSTEM, CONTROL METHOD, AND STORAGE MEDIUM

(71) Applicant: CANON KABUSHIKI KAISHA, Tokyo (JP)

(72) Inventor: Masahiro Abe, Yamato (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 874 days.

(21) Appl. No.: 14/661,100

(22) Filed: Mar. 18, 2015

(65) Prior Publication Data

US 2015/0281685 A1 Oct. 1, 2015

(30) Foreign Application Priority Data

Mar. 27, 2014 (JP) .................................. 2014-066809

(51) Int. Cl.
*A61B 6/00* (2006.01)
*H04N 17/00* (2006.01)

(52) U.S. Cl.
CPC .............. *A61B 6/586* (2013.01); *A61B 6/461* (2013.01); *A61B 6/463* (2013.01); *A61B 6/5294* (2013.01); *H04N 17/002* (2013.01)

(58) Field of Classification Search
CPC ....... A61B 6/461; A61B 6/463; A61B 6/5294; A61B 6/586
See application file for complete search history.

(56) References Cited

U.S. PATENT DOCUMENTS

| | | | | |
|---|---|---|---|---|
| 2001/0053203 A1* | 12/2001 | Ishii | ........................ | A61B 6/105 378/198 |
| 2004/0186370 A1* | 9/2004 | Ishimitsu | .............. | A61B 6/4494 600/407 |
| 2006/0149598 A1* | 7/2006 | Adachi | ................... | G06Q 50/22 705/2 |
| 2011/0186755 A1* | 8/2011 | Otto | ...................... | A61N 5/1031 250/492.3 |
| 2012/0137241 A1* | 5/2012 | Kurosawa | .............. | A61B 8/465 715/771 |
| 2012/0305790 A1* | 12/2012 | Hanawa | ............... | A61N 5/1043 250/393 |

(Continued)

FOREIGN PATENT DOCUMENTS

| | | |
|---|---|---|
| JP | 2004-073426 A | 3/2004 |
| JP | 2004-097637 A | 4/2004 |
| JP | 2008-073201 A | 4/2008 |

(Continued)

*Primary Examiner* — Chih-Cheng Kao
(74) *Attorney, Agent, or Firm* — Venable LLP

(57) ABSTRACT

A radiation imaging control device has a display control function to output, to a display unit, information indicating display content to be displayed on the display unit in order to cause the display unit to display imaging conditions for radiation imaging and a radiation image obtained by radiation imaging under at least one of the imaging conditions. The control device determines the presence or absence of abnormality concerning radiation imaging, and causes, in the case where the presence of abnormality is determined, a storage unit to store the information indicating display content that is output to the display unit by the display control function at a timing based on the abnormality.

25 Claims, 4 Drawing Sheets

(56) References Cited

U.S. PATENT DOCUMENTS

2014/0098933 A1* 4/2014 Profio .................. A61B 6/03
378/19

FOREIGN PATENT DOCUMENTS

| JP | 2008-149151 A | 7/2008 |
|---|---|---|
| JP | 4883737 | 2/2012 |
| JP | 2012-133767 A | 7/2012 |
| JP | 2013-094504 A | 5/2013 |

* cited by examiner

F I G. 4

401

PATIENT ID:22222
PATIENT NAME:GANON JIRO

TUBE VOLTAGE:120kV
TUBE CURRENT:60mA

REX:10
EI:5

ACC#:12345
DATE AND TIME OF INSPECTION:2013/10/23
COLLECTED TIME:15:39:16

402

403 PATIENT ID:22222
PATIENT NAME:GANON JIRO
DATE OF BIRTH:2000/02/03

404 ACC#:12345

405 CHEST PA/AP
CHEST RL/LR
ABDOMEN PA/AP
ABDOMEN RL/LR

INSPECTION END

CONTROL DEVICE, CONTROL SYSTEM, RADIATION IMAGING SYSTEM, CONTROL METHOD, AND STORAGE MEDIUM

BACKGROUND OF THE INVENTION

Field of the Invention

The present invention relates to a control technique in radiation imaging.

Description of the Related Art

In recent years, X-ray sensors such as a flat panel detector which converts X-ray signals into a digital image and outputs the digital image are being widely used. Japanese Patent No. 4883737 discloses transmitting image data collected by an X-ray imaging system using such a sensor, after checking it on a monitor of an imaging device, to an external PACS (Picture Archiving and Communication System) or the like as digital data. A doctor or engineer checks the transmitted image and makes a diagnosis based on it.

In the case where an appropriate image cannot be collected, for example, due to an abnormality of the system, log information output by the system, for example, is used in order to investigate the causes of the abnormality and eliminate the abnormality. However, there are cases where an effective countermeasure cannot easily be taken, such as a case where the log at the time of the occurrence of the abnormality is insufficient, and a case where analysis of the log itself requires a lot of time. Further, although it is also possible to investigate the causes relying on human memory, it is not easy to eliminate the abnormality, for example, in a case where information is not accurate and includes errors.

The present invention has been devised in view of the problems described above, and the invention facilitates, in the case where abnormality occurs in radiation imaging, elimination of the abnormality.

SUMMARY OF THE INVENTION

According to one aspect of the present invention, there is provided a radiation imaging control device comprising: a display control unit configured to output, to a display unit, information indicating display content to be displayed on the display unit in order to cause display, on the display unit to display, imaging conditions for radiation imaging and a radiation image obtained by radiation imaging under at least one of the imaging conditions and; a determination unit configured to determine the presence or absence of abnormality concerning radiation imaging; and a storage control unit configured to, in the case where the presence of abnormality is determined by the determination unit, cause a storage unit to store the information indicating display content that is output to the display unit by the display control unit at a timing based on the abnormality.

According to another aspect of the present invention, there is provided a radiation imaging control device comprising: a display control unit configured to output, to a display unit, information indicating display content to be displayed on the display unit in order to cause the display unit to display imaging conditions for radiation imaging and a radiation image obtained by radiation imaging under at least one of the imaging conditions; a determination unit configured to determine the presence or absence of abnormality concerning radiation imaging; and a storage control unit configured to cause a storage unit to store the information indicating display content that is output by the display control unit regardless of the presence or absence of abnormality, and controls, in the case where the presence of abnormality is determined by the determination unit, the storage unit to hold the information indicating display content that is output to the display unit by the display control unit and to delete other information at a timing based on the abnormality.

According to still another aspect of the present invention, there is provided a radiation imaging control system comprising: a display control unit configured to output, to a display unit, information indicating display content to be displayed on the display unit in order to cause the display unit to display imaging conditions for radiation imaging and a radiation image obtained by radiation imaging under at least one of the imaging conditions; a determination unit configured to determine the presence or absence of abnormality concerning radiation imaging; and a storage control unit configured to, in the case where the presence of abnormality is determined by the determination unit, cause a storage unit to store the information indicating display content that is output to the display unit by the display control unit at a timing based on the abnormality.

According to yet another aspect of the present invention, there is provided a radiation imaging control system comprising: a display control unit configured to output, to a display unit, information indicating display content to be displayed on the display unit in order to cause display, on the display unit to display, imaging conditions for radiation imaging and a radiation image obtained by radiation imaging under at least one of the imaging conditions; a determination unit configured to determine the presence or absence of abnormality concerning radiation imaging; and a storage control unit configured to cause a storage unit to store the information indicating display content that is output by the display control unit regardless of the presence or absence of abnormality, and controls, in the case where the presence of abnormality is determined by the determination unit, the storage unit to hold the information indicating display content that is output to the display unit by the display control unit and to delete other information at a timing based on the abnormality.

According to still yet another aspect of the present invention, there is provided a radiation imaging system configured to perform radiation imaging, comprising: a radiation imaging unit configured to perform radiation imaging by generating radiation and detecting the radiation using a sensor; a display control unit configured to output, to a display unit, information indicating display content to be displayed on the display unit in order to cause the display unit to display imaging conditions for radiation imaging and a radiation image obtained by radiation imaging under at least one of the imaging conditions; a determination unit configured to determine the presence or absence of abnormality concerning radiation imaging; and a storage control unit configured to, in the case where the presence of abnormality is determined by the determination unit, cause a storage unit to store the information indicating display content that is output to the display unit by the display control unit at a timing based on the abnormality.

According to yet still another aspect of the present invention, there is provided a radiation imaging system configured to perform radiation imaging, comprising: a radiation imaging unit configured to perform radiation imaging by generating radiation and detecting the radiation using a sensor; a display control unit configured to output, to a display unit, information indicating display content to be displayed on the display unit in order to cause the display unit to display imaging conditions for radiation imaging and a radiation image obtained by radiation imaging under at least one of the imaging conditions; a determination unit configured to determine the presence or absence of abnormality concerning radiation imaging; and a storage control unit configured to cause a storage unit to store the information indicating display content that is output by the display control unit regardless of the presence or absence of abnormality, and controls, in the case where the presence of abnormality is determined by the determination unit, the storage unit to hold the information indicating display content that is output to the display unit by the display control unit and to delete other information at a timing based on the abnormality.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 4 is a view showing an example of an image obtained.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

The following embodiments do not intend to confine the invention relevant to the scope of claims. Also, all combinations of the features described in the embodiments are not necessarily included in the solutions of the present invention.

Configuration of Radiation Imaging System

Figure 1:
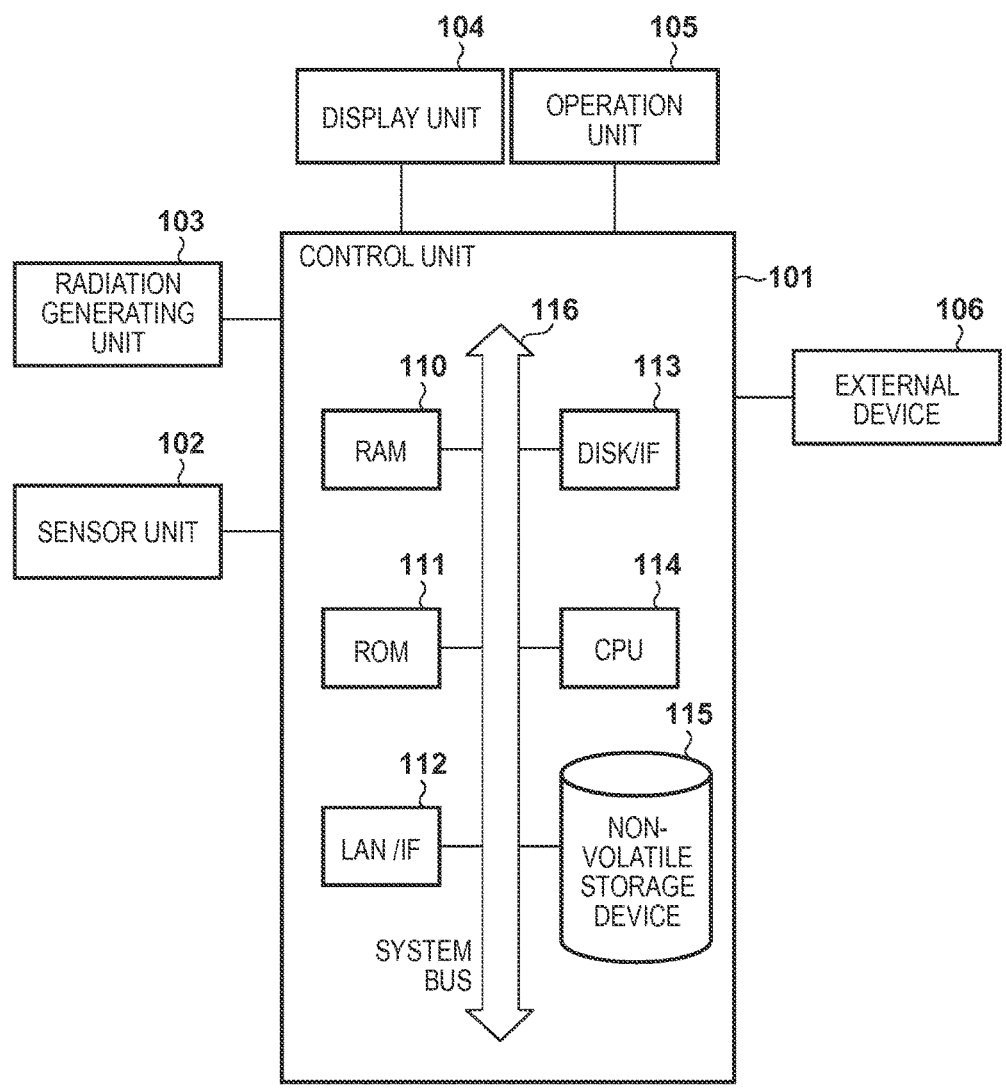
FIG. 1 is a diagram showing an example of a hardware configuration of a radiation imaging system.

FIG. 1 shows an example of a hardware configuration of a radiation imaging system according to this embodiment. As shown in FIG. 1, the radiation imaging system, for example, has a control unit 101, a sensor unit 102, a radiation generating unit 103, a display unit 104, an operation unit 105, and external device 106. It should be noted that these functional units may be independent devices each having separate hardware, or may be included in a single device as a plurality of functional units. Further, the radiation, for example, can be X-rays.

The control unit 101 is a control device that drives the sensor unit or controls the radiation generating unit, based on an input by an operator. Further, the control unit 101 manages various data such as correction data, radiation imaging conditions, and image data. The control unit 101, for example, has a RAM 110, a ROM 111, a LAN interface (LAN/IF) 112, a DISK interface (DISK/IF) 113, a CPU 114, and a non-volatile storage device 115 such as a hard disk, as its components. These hardware components are connected to each other by a system bus 116. That is, the control unit 101 has a general configuration of a computer. The sensor unit 102 is a sensor unit that images radiation signals radiated by the radiation generating unit 103 and passing through a subject, and the collected image is transferred to the control unit 101. The radiation generating unit 103 is a radiation generating device, and emits radiation (radiation in the direction of the subject and the sensor unit 102) based on a command of the control unit 101.

The display unit 104 is constituted, for example, using a general monitor such as a CRT and a liquid crystal display, and displays image data, a GUI (graphical user interface), or the like, on a screen. The operation unit 105 is constituted using input devices such as a mouse, a keyboard, and a radiation switch, and is used to allow an operator (user) to input various commands or data to the control unit 101. In this regard, a monitor having functions of both the display unit 104 and the operation unit 105 such as a touch panel may be used. The external device 106 is an external system, for example, for storing the image transferred from the control unit 101 and displaying it. The external device 106 is implemented, for example, as a PACS (Picture Archiving and Communication System) or a DICOM viewer.

Configuration of Control Unit 101

Figure 2:
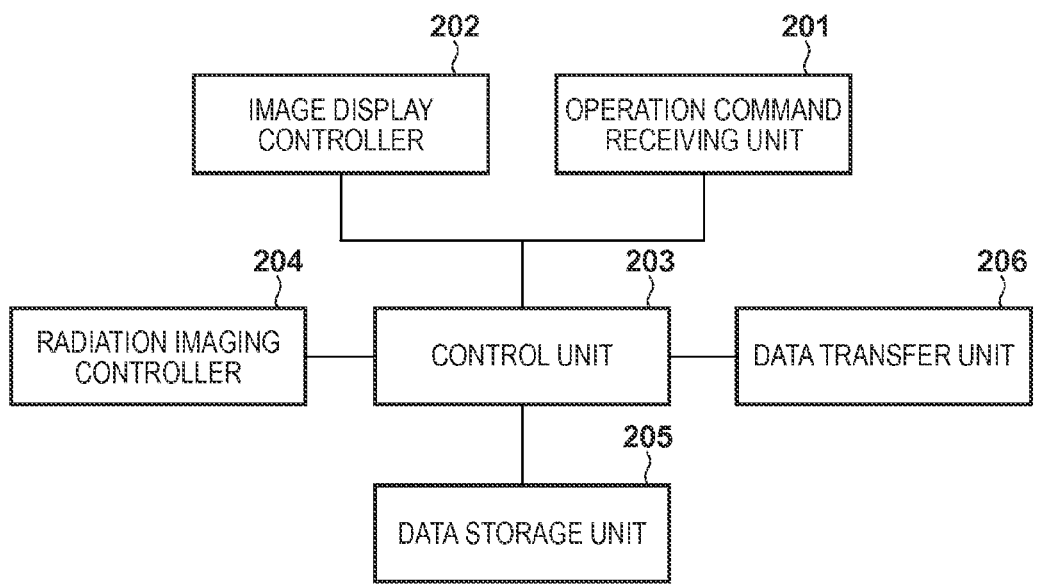
FIG. 2 is a diagram showing an example of a functional configuration of a control unit of the radiation imaging system.

Next, an example of the functional configuration of the aforementioned control unit 101 will be described with reference to FIG. 2. FIG. 2 is a block diagram showing an example of the functional configuration of the control unit 101. As shown in FIG. 2, the control unit 101 has an operation command accepting unit 201, an image display controller 202, a control unit 203, a radiation imaging controller 204, a data storage unit 205, and a data transfer unit 206, for example, as its functions.

The operation command accepting unit 201 is a functional block that accepts various inputs associated with radiation imaging, and accepts patient information, inspection information, or the like, input by an operator (user) using input devices such as a mouse and a keyboard of the operation unit 105. The image display controller 202 controls the display unit 104 to display imaging conditions for radiation imaging and radiographic images (radiation images) obtained by radiation imaging under at least one of the imaging conditions. It should be noted that the control herein is a control, for example, to output information of display content to be displayed in order to cause the display unit 104 to display radiation images, and can be possibly performed even in the state where no image is actually displayed, such as the state where the display unit 104 is turned off. Further, the image display controller 202 may control the display unit 104 to further display an operation GUI (Graphical User Interface).

The control unit 203 has a function to perform radiation imaging by causing various functional blocks to organically cooperate with each other, such as control of the radiation generating device associated with radiation imaging, driving control of the sensor unit, and control of output images. Further, the control unit 203 also can perform other various processes such as obtaining a dose index value associated with radiation imaging, for example, by calculation based on a captured radiation image, or the like, and comparing the value with a pre-set threshold of the dose index value (for example, a value showing a predetermined range for determining the presence or absence of abnormality).

The radiation imaging controller 204, for example, controls the sensor unit 102 and the radiation generating unit 103, causes the radiation generating unit 103 to emit radiation according to a command of the control unit 203, and collects a radiation image from the sensor unit 102 as image data. The data storage unit 205 stores the image data collected, for example, by the radiation imaging controller 204. The data storage unit 205 further stores various data necessary for the radiation imaging system such as a threshold of the dose index value, dose index values calculated concerning radiation imaging, collected screen capture screens, image processing parameters, and calibration data of the sensor. Such data is managed by various storage devices within the control unit 101. The data transfer unit 206 transfers the image data to the external device 106 according to a command from the control unit 203.

In the aforementioned description, an example in which the functional units are implemented as the functions of the control unit 101 is described, but a control system in which at least a part of these functions is implemented by another device in the radiation imaging system may be formed. For example, the image display controller 202 may be included in another device. Of the processes shown below, abnormality detection and storage control may be performed as functions of the control unit 101, and the image display controller 202 may transfer information, for example, according to a command of the control unit 101, so that information indicating output display content is stored in the storage device.

Processing Flow by Control Unit

Figure 3:
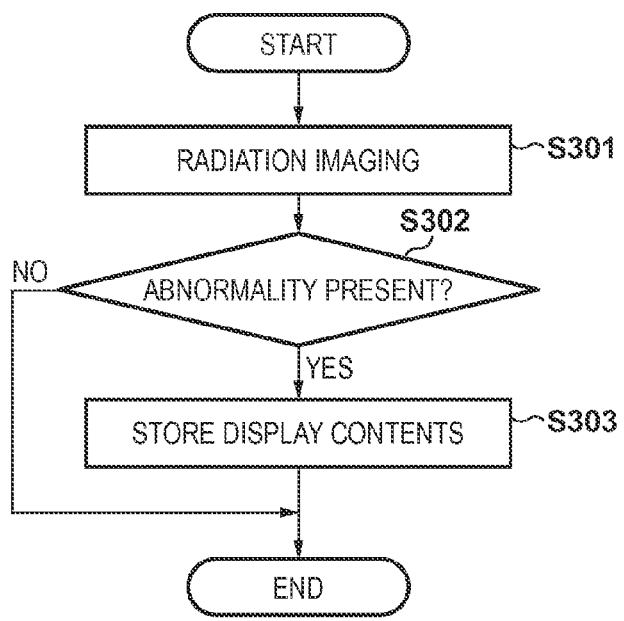
FIG. 3 is a flowchart showing a processing flow of the control unit.

Next, a processing flow that is carried out by the control unit 101 will be described with reference to FIG. 3. In this processing, radiation imaging is first carried out (S301). For example, when an operator (user) inputs a command to require starting radiation imaging through the operation unit 105 (such as an exposure button, a foot switch, or the like), radiation is emitted from the radiation generating unit 103. The sensor unit 102 detects the radiation that has passed through a subject and images it, so that image data is collected. At this time, some imaging conditions for radiation imaging exist, and radiation imaging is performed under at least one of the imaging conditions. The control unit 101 performs display control so that the display unit 104 displays a radiation image as a result of the radiation imaging, and the imaging condition thereof.

The control unit 101 determines the presence or absence of abnormality concerning radiation imaging, while causing the display unit 104 to display the radiation image and the imaging condition thereof (S302). Such determination may be performed by any processing, as long as the processing allows the presence or absence of abnormality concerning radiation imaging to be determined. Some examples will be described later.

The control unit 101 ends the processing as it is, in the case where the absence of abnormality in radiation imaging is determined (NO in S302). On the other hand, in the case where the presence of abnormality in radiation imaging is determined (YES in S302), the control unit 101 obtains information indicating display content to be displayed on the display unit 104 and stores it, according to the determination (S303). In obtaining the information indicating display content, the display content does not need to be actually displayed on the display unit 104. That is, only information on display content that is output to the display unit 104 needs to be obtained, and the display content does not need to be actually displayed on the display unit 104, for example, in the case where a monitor serving as the display unit 104 is turned off due to time-out, or the like. Further, the control unit 101, for example, may obtain information on display content that is to be displayed on the display unit 104, instead of obtaining information on display content after image data or the like obtained in radiation imaging is actually displayed on the display unit 104. This processing also will be described later by way of some processing examples.

In the aforementioned description, the control unit 101 obtains the information on display content after the presence of abnormality concerning radiation imaging is determined, but there is not limitation to this. For example, the configuration may be such that the control unit 101 once obtains information on display content each time imaging is performed, and thereafter it determines the presence or absence of abnormality for the imaging, and deletes the obtained information on display content in the case where no abnormality is detected. That is, the storage control may be such that information, which is output to the display unit 104 concerning radiation imaging in which the presence of abnormality is determined, indicating display content concerning the imaging at the time of occurrence of the abnormality is stored. Accordingly, any processing procedures may be taken to reach such a stage. In the case where the absence of abnormality is determined, information on display content may be obtained, for example, once in 10 times of radiation imaging, instead of obtaining information on display content each time radiation imaging is performed. In the case where the presence of abnormality is determined, the frequency to obtain the information on display content may be thereafter increased (for example, so as to obtain it each time radiation imaging is performed) for a predetermined time period.

There are also probable cases where the image display controller 202 outputs information indicating display content to be displayed to the display unit 104 at constant intervals (for example, 60 frames per second), even if there is no change in the display content to be displayed on the display unit 104. In this case, the configuration may be such that a predetermined number of frames (for example, 3 frames per second) are stored per unit time, for example, instead of storing information indicating display content each time imaging is performed, regardless of the presence or absence of abnormality. Storage control may be such that, after the presence of abnormality concerning radiation imaging is determined, information indicating display content which is output before and after the time of occurrence of the abnormality (one or a predetermined number of frames) is continuously held, and information other than that is deleted. This enables the states before and after the occurrence of the abnormality to be stored. Storage control may be such that information indicating all display content output by the image display controller 202 is stored once, and information other than information indicating display content that is output before and after the time of occurrence of abnormality is deleted.

In the case of the presence of abnormality concerning radiation imaging, the number of frames to be stored per unit time may be increased for a predetermined time period from the time of occurrence of the abnormality. For example, the configuration may be such that, while 3 frames are stored per second at a normal time, 60 frames are stored per second for a predetermined time period from the time when the presence of abnormality is determined. It should be noted that the frequency to store frames may be 1 frame per hour, for example, at a normal time.

The frames to be held may possibly be several frames from the information indicating display content that is output at the time when the presence of abnormality is determined. Further, in the case where there is a time lag from the time when the presence of abnormality is determined to the time when information indicating display content concerning radiation imaging in which the abnormality is present is output, frames to be held may be determined in consideration of the time lag. For example, a predetermined number of frames concerning information indicating display content that is output after the time lag from the time when the presence of abnormality is determined may be held, or a predetermined number of frames concerning information indicating display content that is output further before that may be held.

In either case, storage control is performed so that, in the case of the presence of abnormality concerning radiation imaging, one or a plurality of pieces of information indicating display content that are output to the display unit 104 are stored at a timing based on the time of occurrence of the abnormality.

When information indicating display content concerning the time based on the abnormality is stored, the information indicating display content may be stored after identification information indicating which of one or more abnormalities that have occurred so far corresponds to the information is associated with the information indicating display content. This enables the user to easily recognize which abnormality the stored information indicating display content is associated with, when the user refers to it later. It should be noted that time stamp information may be stored instead of identification information. That is, the information indicating display content may be stored after information that indicates when the information indicating display content is output is associated with the information indicating display content. Thus, the user can easily refer to the information indicating display content by designating the time of occurrence of abnormality.

Examples of Determination Processing

Next, some examples of the determination processing in step S302 will be described. Below, some examples of the determination processing will be individually described, but such examples of processing may be used in combination. Further, the following examples of determination processing are illustrative in all aspects, and the control unit 101 may execute the determination processing using other processing which enables the determination of the presence or absence of abnormality concerning radiation imaging.

EXAMPLE 1

In this example, the control unit 101 determines the presence or absence of abnormality concerning radiation imaging, based on whether or not a dose index value at the time of the radiation imaging is an abnormal value, that is, it falls within a predetermined range. The dose index value herein is an index value, for example, known as an EI (Exposure Index) value. However, an index value other than the EI may be used as long as the index value enables the determination of whether the dose that has reached the detection surface of the sensor is relatively large or small.

In this example, the control unit 101, for example, pre-sets a value (for example, a threshold of the index value) indicating a predetermined range as a reference for determination of an abnormal value, and stores it within the data storage unit 205. The control unit 101 reads out the value indicating the predetermined range from the data storage unit 205 before comparison processing with the dose index value to be obtained concerning actual radiation imaging, for example, before the radiation imaging. On the other hand, the control unit 101 obtains, when the radiation imaging is performed, a dose index value concerning the radiation imaging, for example, by calculation based on image data obtained in the radiation imaging. The control unit 101 compares the thus obtained index value concerning imaging with the value indicating the predetermined range read out from the data storage unit 205. The control unit 101 determines the absence of abnormality concerning radiation imaging in the case where the obtained index value falls within the predetermined range, and determines the presence of abnormality concerning radiation imaging in the case where the obtained index value does not fall within the predetermined range, for example.

EXAMPLE 2

In this example, the control unit 101 determines the presence or absence of abnormality concerning radiation imaging by obtaining the discrepancy between a dose index value obtained concerning current radiation imaging and its statistic value, for example, by calculation based on the statistic value of a plurality of dose index values concerning previous radiation imaging with the same protocol. Here, the index values are the same as those used in Example 1. The control unit 101, for example, obtains an average $\mu$ and a standard deviation $\sigma$ from the data group of index values obtained in previous imaging with the same protocol. The control unit 101 determines the presence or absence of abnormality concerning radiation imaging based on whether or not a dose index value i obtained in current imaging satisfies $\mu-2\sigma \leq i \leq \mu+2\sigma$. The control unit 101 determines the presence of abnormality concerning radiation imaging, for example, in the case where the dose index value i obtained in current imaging does not satisfy the aforementioned formula. It should be noted that the aforementioned formula is not necessarily used, and another method that enables the determination of whether or not the currently obtained value is an abnormal value from statistical dispersion may be used.

EXAMPLE 3

In this example, the control unit 101 determines the presence or absence of abnormality concerning radiation imaging, using results of image processing with respect to the obtained image data. For example, the control unit 101 performs a histogram analysis on the image data obtained by radiation imaging, and determines the presence of abnormality concerning radiation imaging in the case where the subject as an imaging target is determined not to be captured in the image data.

EXAMPLE 4

In this example, the control unit 101 determines the presence or absence of abnormality concerning radiation imaging from the pixel values of the captured image. For example, the control unit 101 determines the presence of abnormality concerning radiation imaging in the case where some pixel values or an average pixel value of coordinates around the center of the captured image is extremely high or low. In the same manner as in Example 1, the control unit 101 can easily determine the presence or absence of abnormality, for example, by setting a value (value indicating the predetermined range) as a comparison target in advance, storing it within the data storage unit 205, and comparing pixel values concerning current imaging with the stored value.

EXAMPLE 5

In this example, the control unit 101 determines the presence or absence of abnormality concerning radiation imaging depending on whether or not a predetermined input is accepted from the user via the operation unit 105. That is, the control unit 101 monitors whether or not the user performs a predetermined input by detecting abnormality, and determines the presence or absence of abnormality depending on the monitored results.

For example, the control unit 101 determines the presence of abnormality concerning certain radiation imaging, in the case where the user issues a command to execute a process for an image of misexposure or re-imaging process concerning the radiation imaging. The process for an image of misexposure and re-imaging process are processing to be carried out, generally, in the case where the user determines the first captured image is inappropriate. Further, such imaging that is determined to be inappropriate is imaging, for example, in which a region that is normally expected to show up does not show up, the subject is blurred, or wrong imaging conditions are used.

In this way, the presence of abnormality is determined in the case where the process for an image of misexposure or re-imaging process is performed, and information indicating display content to be displayed that is output to the display unit 104 is obtained, thereby allowing the user to verify the situation where the misexposure has occurred by referring to the display content again later.

It should be noted that the control unit 101 may determine the presence of abnormality also in the case where an operational input other than the process for an image of misexposure or re-imaging process is accepted. For example, the control unit 101 may determine the presence of abnormality in the case where an input to adjust image processing parameters is received. This enables the control unit 101, in the case where an image is disturbed as a result of the adjustment of image processing parameters, to obtain information indicating display content to be displayed that is output to the display unit 104 at that time, thereby allowing the user, for example, to review the setting of the parameters.

EXAMPLE 6

In this example, the control unit 101 determines the presence or absence of abnormality concerning radiation imaging depending on whether or not abnormality occurs in the operation of the radiation imaging system, instead of determining the presence or absence of abnormality from captured images. In this way, the control unit 101 can record the situation when the abnormality occurs by obtaining information on display content to be displayed that is output to the display unit 104 in the case where abnormality occurs in the system.

Examples of Information to be Stored

Next, some examples of information to be obtained by the control unit 101 in the case where the presence of abnormality is determined will be described. It should be noted that the following information is illustrative in all aspects, and the control unit 101 may perform storage control so that other information, output to the display unit 104, concerning display content to be displayed on the display unit 104 is stored.

EXAMPLE 1

In this example, the control unit 101 obtains, as information indicating display content, a screen capture of a screen displayed on the display unit 104 when the presence of abnormality is determined. The obtained screen capture is stored in the data storage unit 205 as image data. The screen capture can possibly be information indicating display content that is output to the display unit 104 in order to cause the display unit 104 to display an image, instead of being an image actually displayed on the display unit 104. That is, the information indicating display content is not required to be displayed on the display unit 104. Further, the information indicating display content is information from which an image of the display content to be displayed is reproduced at any time by inputting, to a display device (which is not limited to the display unit 104), signals (bit columns) that are produced and output to cause the display unit 104 to display the image.

It should be noted that a screen capture may include or not include a radiation image itself obtained in radiation imaging. That is, information from which imaging conditions, or the like, at the time when abnormality occurs can be seen is satisfactory, and information indicating display content including imaging conditions without including a radiation image may be obtained. It should be noted that the screen capture may be a screen capture including an entire GUI screen to be displayed on the display unit 104, or may be an image in which only a part of display content to be displayed on the display unit 104 that indicates the situation of radiation imaging is extracted.

FIG. 4 shows an example of a screen capture to be obtained. In FIG. 4, the reference numeral 401 denotes an entire operation screen, and the reference numeral 402 denotes an image display region. FIG. 4 shows an appearance in which the subject is not properly depicted in the image display region 402 as a result of abnormal radiation imaging. On the other hand, annotation information is depicted at four corners the display region, where attribute information, or the like, in the radiation imaging is displayed. For example, it can be seen from the annotation on the lower left that this imaging was performed at 15:39:16 on Oct. 23, 2013. The reference numeral 403 denotes a patient information display region in which information on a patient as a subject of inspection is displayed. The reference numeral 404 denotes an inspection information display unit, and the example of FIG. 4 shows the case where Accession number to identify the inspection is 12345. Further, the reference numeral 405 denotes a protocol display unit. The protocol display unit 405 shows sites to be imaged and results after the imaging. The result image is displayed on the protocol display unit 405 other than the image display region 402, regardless of the presence or absence of abnormality concerning radiation imaging. The example of FIG. 4 shows that the current imaging is an inspection in which four sites of chest PA/AP, chest RL/LR, abdomen PA/AP, abdomen RL/LR are planned to be imaged. Further, the second imaging from the top of chest RL/LR matches the display image shown in the image display region 402 captured when the presence of abnormality is determined. Therefore, the user can easily recognize that some abnormality has occurred in the imaging of chest RL/LR by referring to the screen capture.

EXAMPLE 2

As shown in FIG. 4, the operation screen may include personal information such as patient ID and patient name by which a person is specified in some cases. Therefore, in this example, the control unit 101 obtains, as information indicating display content, an image that is processed so that a part of the screen capture that includes personal information isn't visually perceptible and stores it within the data storage unit 205.

Figure 5:
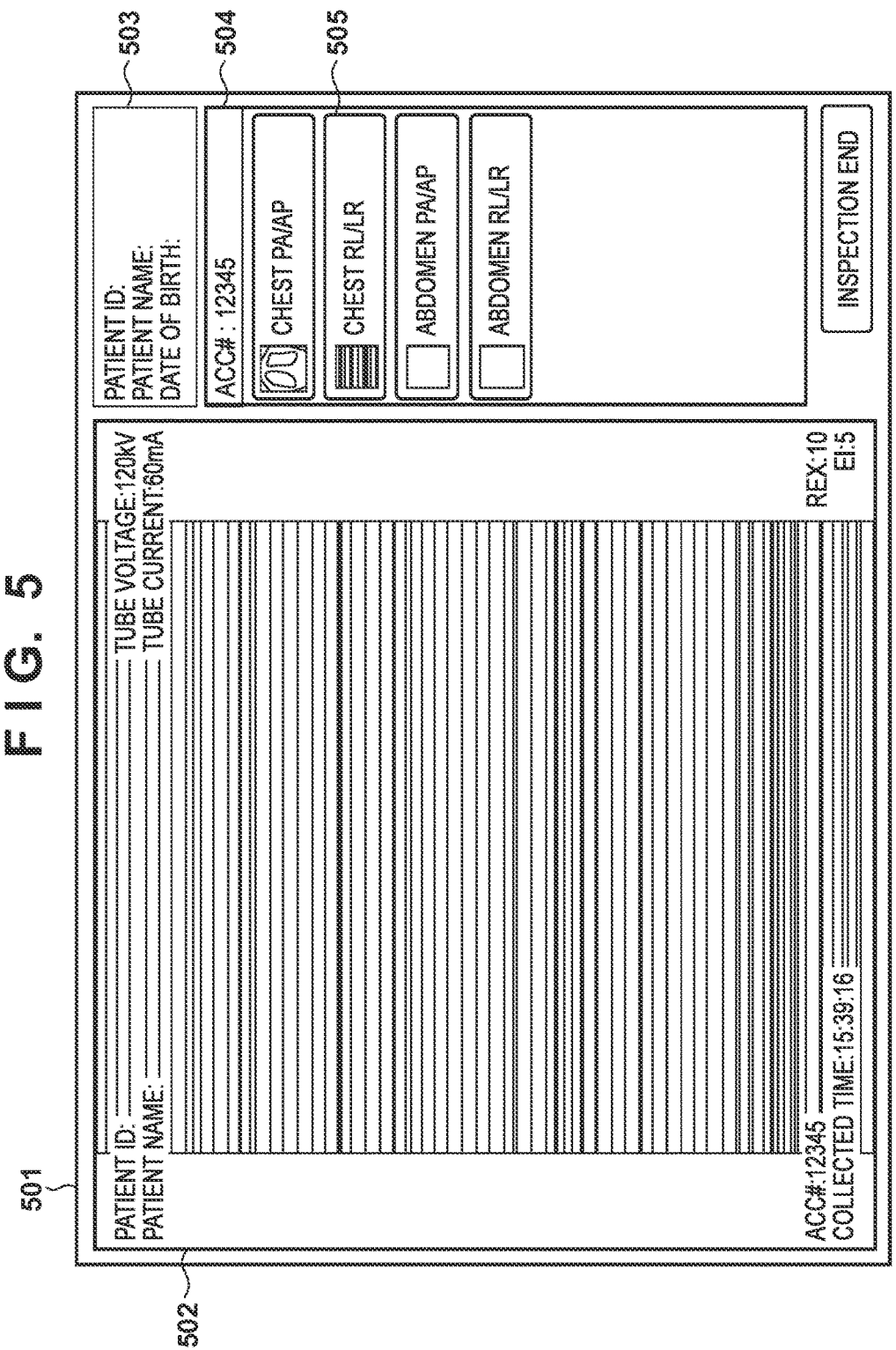
FIG. 5 is a view showing another example of an image obtained.

FIG. 5 shows an example of the screen capture processed so that a part of personal information isn't visually perceptible. In the example of FIG. 5, as different from the example of FIG. 4, patient ID and patient name are removed from the annotation region on the upper left that is displayed in an image display region 502. Further, in the example of FIG. 5, patient ID, patient name, the date of birth are deleted from a patient information display region 503. In this way, the protection of personal information is enabled by storing an image that has been processed so that personal information isn't visually perceptible.

Others

The control unit 101 may obtain information concerning radiation imaging such as sensor information, log data, image data, date and time of inspection, Study Instance UID, Service Object Pair (SOP) Instance UID, and image processing parameters, in addition to the information indicating display content. The UID is Unique Identifier, and the Study Instance UID and the SOP Instance UID are ID numbers defined by the DICOM standard. The control unit 101 obtains such information in addition to the information indicating display content, thereby allowing the user to easily perform subsequent analysis of abnormality. Further, the storing process may be performed so that analysis data is collectively stored in folders, or the like, based on the date and time of occurrence, in consideration of collection of the analysis data.

In this way, in the case where abnormality concerning radiation imaging occurs and a normal image cannot be collected due to errors, the control unit 101 according to this embodiment stores information indicating display content that is output at a timing based on the abnormality. This allows the user to easily recognize the content of a screen displayed at the time of occurrence of the abnormality, which makes it easy to eliminate the abnormality.

The present invention makes it easy to eliminate abnormality, when the abnormality occurs in radiation imaging.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-066809, filed Mar. 27, 2014, which is hereby incorporated by reference herein in its entirety.

What is claimed is:

1. An X-ray radiation imaging control device comprising:
    a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions;
    a determination unit configured to determine the presence or absence of abnormality concerning X-ray radiation imaging based on a dose index value derived from image data for the X-ray radiation image; and
    a storage control unit configured to cause a storage unit to store the information indicating display content that is output to the display unit by the display control unit at a timing based on the abnormality in the case where the presence of abnormality is determined by the determination unit.

2. The control device according to claim 1, wherein the storage control unit causes the storage unit to store predetermined pieces of the information indicating display content that is output to the display unit by the display control unit at a time after the time when the occurrence of the abnormality is determined.

3. The control device according to claim 1, wherein the storage control unit causes the storage unit to further store predetermined pieces of the information indicating display content that is output to the display unit by the display control unit at a time before the time when the occurrence of the abnormality is determined.

4. The control device according to claim 1, wherein the storage control unit obtains, in response to the determination of the presence of abnormality by the determination unit, the information indicating display content that is output to the display unit by the display control unit at a timing based on the time when the occurrence of the abnormality is determined and causes the storage unit to store the information.

5. The control device according to claim 1, wherein the storage control unit causes the storage unit to store the information indicating display content that is output by the display control unit regardless of the presence or absence of abnormality, and
    controls the storage unit to hold the information indicating display content that is output to the display unit by the display control unit at the timing based on the abnormality and to delete other information.

6. The control device according to claim 5, wherein the storage control unit causes the storage unit to store the information indicating display content that is output by the display control unit each time X-ray radiation imaging is performed regardless of the presence or absence of abnormality.

7. The control device according to claim 5, wherein the storage control unit causes the storage unit to store the information indicating display content that is output by the display control unit at constant intervals regardless of the presence or absence of abnormality.

8. The control device according to claim 1, wherein the information indicating display content includes a screen capture of a screen to be displayed on the display unit.

9. The control device according to claim 1, wherein the information indicating display content includes a screen capture of an image including the X-ray radiation image to be displayed on the display unit.

10. The control device according to claim 1, wherein the information indicating display content includes an image processed so that a part of a screen capture of a screen to be displayed on the display unit is not visually perceptible.

11. The control device according to claim 1, wherein the storage control unit causes the storage unit to further store at least one of information of a sensor used for X-ray radiation imaging, log data, image data, date and time of inspection, Study Instance Unique Identifier (UID), and Service Object Pair (SOP) Instance UID.

12. The control device according to claim 1, wherein the determination unit determines the presence or absence of abnormality concerning X-ray radiation imaging depending on whether or not a dose index value in the X-ray radiation imaging falls within a predetermined range.

13. The control device according to claim 1, wherein the determination unit determines the presence or absence of abnormality in current X-ray radiation imaging based on a comparison between a statistic value of dose index values in previous X-ray radiation imaging and a dose index value in the current X-ray radiation imaging.

14. The control device according to claim 1, wherein the determination unit determines the presence or absence of abnormality concerning X-ray radiation imaging depending on the presence or absence of abnormality relating to operation of an X-ray radiation imaging system including the control device when the X-ray radiation imaging is performed.

15. The control device according to claim 1, further comprising an accepting unit configured to accept an input from a user, wherein
the determination unit determines the presence or absence of abnormality concerning X-ray radiation imaging depending on whether or not the accepting unit accepts a predetermined input concerning the X-ray radiation imaging.

16. An X-ray radiation imaging control device comprising:
a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions;
a determination unit configured to determine the presence or absence of abnormality concerning X-ray radiation imaging based on a dose index value derived from image data for the X-ray radiation image; and
a storage control unit configured to cause a storage unit to store the information indicating display content that is output by the display control unit regardless of the presence or absence of abnormality, and controls the storage unit to hold the information indicating display content that is output to the display unit by the display control unit and to delete other information at a timing based on the abnormality in the case where the presence of abnormality is determined by the determination unit.

17. An X-ray radiation imaging system configured to perform X-ray radiation imaging, comprising:
an X-ray radiation imaging unit configured to perform X-ray radiation imaging by generating X-ray radiation and detecting the X-ray radiation using a sensor;
a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions;
a determination unit configured to determine the presence or absence of abnormality concerning X-ray radiation imaging based on a dose index value derived from image data for the X-ray radiation image; and
a storage control unit configured to cause a storage unit to store the information indicating display content that is output to the display unit by the display control unit at a timing based on the abnormality in the case where the presence of abnormality is determined by the determination unit.

18. An X-ray radiation imaging system configured to perform X-ray radiation imaging, comprising:
an X-ray radiation imaging unit configured to perform X-ray radiation imaging by generating X-ray radiation and detecting the X-ray radiation using a sensor;
a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions;
a determination unit configured to determine the presence or absence of abnormality concerning X-ray radiation imaging based on a dose index value derived from image data for the X-ray radiation image; and
a storage control unit configured to cause a storage unit to store the information indicating display content that is output by the display control unit regardless of the presence or absence of abnormality, and controls the storage unit to hold the information indicating display content that is output to the display unit by the display control unit and to delete other information at a timing based on the abnormality in the case where the presence of abnormality is determined by the determination unit.

19. A method for controlling an X-ray radiation imaging system including a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions, the method comprising:
determining the presence or absence of abnormality concerning X-ray radiation imaging based on a dose index value derived from image data for the X-ray radiation image; and
causing a storage unit to store the information indicating display content that is output to the display unit by the display control unit at a timing based on the abnormality in the case where the presence of abnormality is determined in the determination step.

20. A method for controlling an X-ray radiation imaging system including a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions, the method comprising:

determining the presence or absence of abnormality concerning X-ray radiation imaging based on a dose index value derived from image data for the X-ray radiation image; and causing a storage unit to store the information indicating display content that is output by the display control unit regardless of the presence or absence of abnormality, and controlling the storage unit to hold the information indicating display content that is output to the display unit by the display control unit and to delete other information at a timing based on the abnormality in the case where the presence of abnormality is determined in the determination step.

21. A non-transitory computer-readable storage medium storing a computer program for causing a computer, which is included in an X-ray radiation imaging control device and has a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions, to:

determine the presence or absence of abnormality concerning X-ray radiation imaging based on a dose index value derived from image data for the X-ray radiation image; and cause a storage unit to store the information indicating display content that is output to the display unit by the display control unit at a timing based on the abnormality in the case where the presence of abnormality is determined in the determination.

22. A non-transitory computer-readable storage medium storing a computer program for causing a computer, which is included in an X-ray radiation imaging control device and has a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions, to:

determine the presence or absence of abnormality concerning X-ray radiation imaging based on a dose index value derived from image data for the X-ray radiation image; and cause a storage unit to store the information indicating display content that is output by the display control unit regardless of the presence or absence of abnormality, and control the storage unit to hold the information indicating display content that is output to the display unit by the display control unit and to delete other information at a timing based on the abnormality in the case where the presence of abnormality is determined in the determination step.

23. An X-ray radiation imaging control device comprising:

a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions;

a determination unit configured to determine the presence or absence of abnormality concerning X-ray radiation imaging based on the presence or absence of executing a misexposure or re-imaging process; and a storage control unit configured to cause a storage unit to store the information indicating display content that is output to the display unit by the display control unit at a timing based on the abnormality in the case where the presence of abnormality is determined by the determination unit.

24. An X-ray radiation imaging control device comprising:

a display control unit configured to output, to a display unit, information indicating display content to be displayed on the display unit in order to cause the display unit to display imaging conditions for X-ray radiation imaging and an X-ray radiation image obtained by X-ray radiation imaging under at least one of the imaging conditions;

a determination unit configured to determine the presence or absence of abnormality concerning X-ray radiation imaging based on the presence or absence of executing a misexposure or re-imaging process; and a storage control unit configured to cause a storage unit to store the information indicating display content that is output by the display control unit regardless of the presence or absence of abnormality, and controls the storage unit to hold the information indicating display content that is output to the display unit by the display control unit and to delete other information at a timing based on the abnormality in the case where the presence of abnormality is determined by the determination unit.

25. The control device according to claim 24, wherein a user issues a command to execute the misexposure or re-imaging process.

* * * * *